(12) United States Patent
Kayser et al.

(10) Patent No.: US 6,943,006 B2
(45) Date of Patent: Sep. 13, 2005

(54) METHOD FOR METABOLIZING CARBAZOLE IN PETROLEUM

(75) Inventors: Kevin J. Kayser, Chesterfield, MI (US); John J. Kilbane, II, Woodstock, IL (US)

(73) Assignee: Alps Electric Co., Ltd., Tokyo (JP)

( * ) Notice: Subject to any disclaimer, the term of this patent is extended or adjusted under 35 U.S.C. 154(b) by 0 days.

(21) Appl. No.: 10/658,691

(22) Filed: Sep. 9, 2003

(65) Prior Publication Data

US 2004/0110258 A1 Jun. 10, 2004

Related U.S. Application Data

(60) Provisional application No. 60/409,562, filed on Sep. 10, 2002.

(51) Int. Cl.$^7$ .............................. C12N 1/20; C12N 1/21; C12N 9/02; C12P 13/00; C12P 7/02
(52) U.S. Cl. ............................ 435/252.1; 435/252.3; 435/128; 435/155; 435/189
(58) Field of Search .......................... 435/252.1, 128, 435/155, 189

(56) References Cited

U.S. PATENT DOCUMENTS

| | | | | |
|---|---|---|---|---|
| 3,276,840 A | * | 10/1966 | Gonzalo | 422/1 |
| 5,856,167 A | * | 1/1999 | Outtrup | 435/221 |
| 5,888,797 A | * | 3/1999 | Outtrup | 435/221 |
| 5,928,929 A | * | 7/1999 | Outtrup et al. | 435/221 |

OTHER PUBLICATIONS

Sato et al., "Cloning of genes involved in carbazole degradation of Pseudomonas sp. strain CA10: nucleotide sequences of genes and characterization of meta–cleavage enzymes and hydrolase," J Bacteriology 179(15):4841–4849, 1997.*

Enzyme Nomenclature (on–line), record for subtilisin (EC 3.4.21.62), published by Nomenclature Committee of the International Union of Biochemistry and Molecular Biology (NC–IUBMB), http://www.chem.qmul.ac.uk/iubmd/enzyme, printed Jun. 24, 2004.*

Kilbane et al., "Isolation and characterization of Sphingomonas sp. GTIN11 capable of carbazole metabolism in petroleum," Biochem Biophys Res Comm 297(2):242–248, available on line Sep. 4, 2002.*

Ouchiyama, Naoki et al., "Cloning and Nucleotide Sequence of Carbazole Catabolic Genes from *Pseudomonas stutzeri* strain OM1, Isolated from Activated Sludge", *J. Gen. Appl. Microbiol.*, 44, 57–63 (1998).

Shotbolt–Brown, J. et al., "Isolation and Description of Carbazole–Degrading Bacteria", *Can. J. Microbiol.*, 42 79–82 (1996).

Schneider, J. et al., "Biodegradation of Carbazole by *Ralstonia* sp. RJGII. 123 isolated From a Hydrocarbon Contaminated Soil", *Can. J. Microbiol.*, 46 269–277 (2000).

(Continued)

*Primary Examiner*—Robert Wax
*Assistant Examiner*—Rosanne Kosson
(74) *Attorney, Agent, or Firm*—Brinks Hofer Gilson & Lione

(57) ABSTRACT

A method for selective cleavage of C—N bonds genes that encode for at least one enzyme suitable for conversion of carbazole to 2-aminobiphenyl-2,3-diol are combined with a gene encoding an amidase suitable for selectively cleaving a C—N bond in 2-aminobiphenyl-2,3-diol, forming an operon that encodes for cleavage of both C—N bonds of said carbazole. The operon is inserted into a host culture which, in turn, is contacted with the carbazole, resulting in selective cleavage of both C—N bonds of the carbazole. Also disclosed is a new microorganism that expresses a carbazole degradation trait constitutively and a method for degrading carbazole employing this microorganism.

5 Claims, 2 Drawing Sheets

OTHER PUBLICATIONS

Ouchlyama, N. et al., "Biodegradation of Carbazole by *Pseudomonas* spp. CA06 and CA10", *Biosci. Biotech. Biochem.*, 57 (3), 455–460 (1993).

Hisatsuka, K. et al., "Microbial Transformation of Carbazole to Anthranilic Acid by *Pseudomones stutzen*", *Biosci. Biotech. Biochem.*, 58 (1), 213–214 (1994).

Shao, Z. Q. et al., "Cloning and Expression of the s–Triazine Hydrolase Gene (trzA) from *Rhodococcus corallinus* and Development of *Rhodococcus* Recombinant Strains Capable of Dealkylating and Dechlorinating the Herbicide Atrazine", *Journal of Bacteriology*, vol. 177, No. 20, pp. 5748–5755 (Oct. 1995).

Trott, S. et al., "Cloning and Heterologous Expression of an Enantioselective Amidase from *Rhodococcus erythropolis* Strain MP50", *Applied and Environmental Microbiology*, vol. 68, No. 7, pp. 3279–3286 (Jul. 2002).

Grosser, R. J. et al., "Indigenous and Enhanced Mineralization of Pyrene, Benzo[a]pyrene, and Carbazole in Soils", *Applied and Environmental Microbiology*, vol. 57, No. 12, pp. 3462–3469 (Dec. 1991).

Lasa, I. et al., "Development of *Thermus–Escherichia* Shuttle Vectors and Their Use for Expression of the *Clostridium thermocellum celA* Gene in *Thermus thermophilus*", *Journal of Bacteriology*, vol. 174, No. 20, pp. 6424–6431 (Oct. 1992).

Aronstein, B. N. et al., "Biological and Integrated Chemical–Biological Treatment of PCB Congeners in Soil/Sediment–Containing Systems", *J. Chem. Tech. Biotechnol.*, 63, 321–326 (1995).

Kilbane II, J. J. et al., "Selective Removal of Nitrogen from Quinoline and Petroleum by *Pseudomones ayucide* IGTN9m", *Applied Environmental Microbiology*, vol. 66, No. 2, pp. 688–693 (Feb. 2000).

Nojiri, H. et al., "Genetic Characterization and Evolutionary Implications of a car Gene Cluster in the Carbazole Degrader *Pseudomones* sp. Strain CA10", *Journal of Bacteriology*, vol. 183, No. 12, pp. 3663–3679 (Jun. 2001).

Kayser, K. J. et al., "Utilization of Organosulphur Compounds by Axenic and Mixed Cultures of *Rhodococcus rhodochrous* IGTS8" *Journal of General Microbiology*, 139, 3123–3129 (1993).

Watson, G. K. et al., "Microbial Metabolism of the Pyridine Ring—Metabolic Pathways of Pyridine Biodegradation by Soil Bacteria", *Biochem. J.*, 146, 157–172 (1975).

Furukawa, K. et al., "Cloning of a Gene Cluster Encoding Biphenyl and Chlorobiphenyl Degradation in *Pseudomonas pseudoalcaligenes*", *Journal of Bacteriology*, vol. 166, No. 2, pp. 392–398 (May 1986).

Reese, M. G. et al., "Large Scale Sequencing Specific Neural Networks for Promoter and Splica Site Recognition", *Pacific Symposium on Biocomputing*, pp. 737–738, (Jan. 3–6, 1996).

Shepherd, J. M. et al., "Novel Carbazole Degradation Genes of *Sphingomonas* CB3: Sequence Analysis, Transcription, and Molecular Ecology" *Biochemical and Biophysical Research Communications*, 247, 129–135 (1998).

Nojiri, H. et al., "Organization and Transcriptional Characterization of Catechol Degradation Genes Involved in Carbazole Degradation by *Pseudomonas resinovorans* Strain CA10" *Biosci. Biotechnol. Biochem.*, 66 (4), 897–901 (2002).

Kirimura, K. et al., "Selective and Continuous Degradation of Carbazole Contained in Petroleum Oil by Resting Cells of *Sphingomonas* sp CDH–7", *Biosci. Biotechnol. Biochem.*, 63 (9), 1563–1568 (1999).

Loh, K. et al., "Kinetics of Carbazole Degradation by *Pseudomonas putide* in Presence of Sodium Salicylate", *Wat. Res.*, vol. 34, No. 17, pp. 4131–4138 (2000).

Ellis, L. B. M. et al., "The University of Minnesota Biocatalysis/Biodegradation Degradation: Emphasizing Enzymes", *Nucleic Acids Research*, vol. 29, No. 1, pp. 340–343, (2001).

Maidak, B. L. et al., "The RDP–II (Ribosomal Database Project)", *Nucleic Acids Research*, vol. 29, No. 1, pp. 173–174 (2001).

Habe, H. et al., "*Sphingomonas* sp. Strain KA1, Carrying a Carbazole Dioxygenase Gene Homologue, Degrades Chlorinated Dibenzo–p–dioxins in Soil", *FEMS Microbiology Letters* 211 43–49 (2002).

Sato, S. Et al., "Identification and Characterization of Genes Encoding Carbazole 1,9a–Dioxygenase in *Pseudomonas* sp. Strain CA10", *Journal of Bacteriology*, vol. 179, No. 15, pp. 4850–4858, (Aug. 1997).

* cited by examiner

SEQUENCE LISTING

<160> NUMBER OF SEQ ID NOS: 4

<210> SEQ ID NO 1
<211> LENGTH: 1137
<212> TYPE: DNA
<213> ORGANISM: Sphingomonas sp.

<400> SEQUENCE: 1

```
gtggctaacc aaccatcaat cgccgagcgc agaaccaagg tttgggagcc ttatatccgt      60
gcgaaactcg ggttccgaaa ccattggtat cccgttcgcc tcgcgagcga aatcgccgaa     120
ggtactcccg ttcccgtcaa gctcctggga gagaagattc tgctcaatcg cgtgggcggc     180
aaggtctatg cgatccagga caggtgcctg catcgcggtg taacgctttc cgaccgggtc     240
gagtgctatt ccaagaacac catatcctgc tggtatcacg gctggacata tcgctgggac     300
gatgccgcc tcgtcgatat cctcacaaac cccggcagtg tgcagatcgg ccggcgcgct     360
ttgaagacgt tcccggttga agaggccaaa ggtcttatct tcgtttacgt aggcgacggc     420
gaaccaacgc cgcttatcga agatgtgccg cccggcttcc ttgatgaaaa ccgcgccatt     480
cacggccaac atcggctcgt ggcctcgaac tggcgcttgg gtgcggaaaa cggctttgat     540
gcggggcacg tcttcattca caagaattcg atcctggtga aggcaacga tatcattctg     600
ccgcttggct ttgcgcctgg cgatcccgac cagcttacgc gttccgaggt tgctgcgggc     660
aagcccaaag gtgtttacga tctgcttggc gagcattcgg tgccggtttt cgaaggcatg     720
atcgaaggca aacctgcaat ccatggcaac attggcagca agcgcgtcgc catcagcata     780
tcgatctggc tgccgggcgt actcaaggtc gaaccgtggc cggatcccga gctcacgcag     840
ttcgaatggt acgtgccggt cgatgagacc agccacctct acttccagac gctgggcaaa     900
gtcgtgacgt caaaggaagc ggcagactcc ttcgagcgag aattccacga aaaatgggta     960
ggcctcgcgc ttaacggctt caatgatgac acatcatgg cacgtgaatc gatggagccg    1020
ttctacgctg atgatcgcgg ttggtccgaa gaaatcctgt tcgagccgga ccgcgcaatc    1080
atcgagtggc gggggcttgc cagtcagcac aatcgcggca ttcaggaagc acgttga      1137
```

<210> SEQ ID NO 2
<211> LENGTH: 330
<212> TYPE: DNA
<213> ORGANISM: Sphingomonas sp.

<400> SEQUENCE: 2

```
atgaccgcaa aggtccgcgt gatcttccgc gcagccggcg gcttcgagca tctggtcgaa      60
accgaagcgg gagtatcgct catggaagcg gccgttctga acggcgtgga cggtatcgaa     120
gccgtttgcg ggggcgcctg tgcctgcgcc acgtgccacg tttacgttgg ccccgagtgg     180
ctagatgcgc tgaaaccgcc gagtgagacc gaagacgaaa tgctcgattg cgtagcggaa     240
cgtgcgccgc attcgcggct gtcctgccag atccgcctta ccgacctgct cgacggcctg     300
accctggaac tgccgaaggc acagtcatga                                      330
```

<210> SEQ ID NO 3
<211> LENGTH: 990
<212> TYPE: DNA
<213> ORGANISM: Pseudomonas resinovorans

<400> SEQUENCE: 3

```
atgtaccaac tcaaaattga agggcaagcg ccagggacct gcggctcagg gaagagcctg      60
```

-continued

| | | |
|---|---|---|
| ttggtctcag cacttgctaa tggtatcgga tttccgtacg agtgtgcatc gggaggttgc | 120 |
| ggagtatgca aattcgagtt actcgaaggg aatgtccaat caatgtggcc ggatgctcca | 180 |
| ggactttctt cgcgagatcg tgagaagggc aaccgccatc ttgcatgcca gtgcgttgcg | 240 |
| ctctcagacc tgcggatcaa agtcgcagtg caggacaagt acgtcccaac gattccaatc | 300 |
| tcaagaatgg aagcggaagt tgttgaggtc cgggcgctaa ctcatgacct gctgtccgtg | 360 |
| cgattacgca ctgatgggcc agcaaatttc ctccccggcc agttctgcct agtagaggca | 420 |
| gagcagttgc caggcgtggt tcgcgcatat tcaatggcga atttaaagaa ccccgaaggc | 480 |
| atatgggagt tctatattaa gagggtaccc acaggacgat ttagtccttg gcttttcgaa | 540 |
| aatagaaaag aaggcgctcg tctattttg acgggaccaa tgggcacatc tttcttccgt | 600 |
| ccagggaccg gccgaaagag tctttgcatt ggcggcggtg ccgggctctc gtatgcggcc | 660 |
| gctattgcac gcgcctcgat gcgcgaaaca gacaagccgg taaagttgtt ctacggctca | 720 |
| agaactccgc gcgacgctgt tcggtggatc gatatcgaca tcgatgagga caagcttgag | 780 |
| gtcgtccagg cagttacgga agacacggat agcctttggc aagggcccac tggttttatt | 840 |
| catcaggttg tcgacgcagc gctgcttgaa accctaccgg aatacgaaat ttatcttgcc | 900 |
| ggtccaccgc ctatggtcga cgctactgtc cgtatgctgc tcggcaaggg tgttccacgc | 960 |
| gatcaaattc attttgacgc attttttctaa | 990 |

<210> SEQ ID NO 4
<211> LENGTH: 1578
<212> TYPE: DNA
<213> ORGANISM: Rhodococcus erythropolis

<400> SEQUENCE: 4

| | | |
|---|---|---|
| gtgcgaccca atcgcccatt cggccatgtc cgcccgccga cagccgaaca gctccaggag | 60 |
| tacagcgccc gccaccactt cgacctcgac gaggaactgg ccgcccagct cgttccggtc | 120 |
| gtggcggaga tggtgactgc cttcgacctg atcgacgaac taccgcaacc gccgcagccg | 180 |
| ccgacgccgt acacggaccg cgacatcggc cgcgaaccga ccggcgacga agacccgttc | 240 |
| aacgcattca tccggttctg ccgggtggag ggcgccacgg aggggccact gagcgacctg | 300 |
| accgccgcga tcaaggactg catcgccatc gccgtatgc ccaccacgaa cgggtcccgg | 360 |
| atgctcccga ctgtgatcgc caccgaggat gccgtggtgg tggagcggct gctcgcggca | 420 |
| ggcgccacca tcgtcggcaa gacgaacctc gaggacatgg cgatgggtat cggtgaaggc | 480 |
| agcgtctacg gtcctgcgct gaacccgaac aaccccgccc acggcacggg tggatcttcc | 540 |
| agcggctccg gcgctgccgt cgctgccggc atggtcgact cgccctgggg cgtcgatgag | 600 |
| gcaggcagca tccggatccc ggccgcatgg tgcggactgg tcggcatgaa ggcgacccac | 660 |
| ggcctggtgc cgtcttacgg cctgacatac atggaccaca ccttggacca catcgggccc | 720 |
| atcaccaggg gggtcgagct caacgcccgg gtcctcgagg tgttggccgg ggccgactgg | 780 |
| cgcgaccctc agtgggtgcg taaccttccg gagccggaga actacggctc cgcgctcggc | 840 |
| gagggagtat ccggtctgag attcgcggtc gtcgaggagt cactggagcc gaacggtgcg | 900 |
| acgccggacg tgatcgccgc gttcaaccag ggactggcgg cgctcgagag cgccggtgcg | 960 |
| accatcgagc gggtctcggt gccgttgtgg acggcggcct ggcctatcca gagcggcgtg | 1020 |
| atggctttca acgcgcgcgc tatggcggac tccgccggtg tgggctactt ccacaagggg | 1080 |
| cgcgtggacg tcagcaccgc cgtcacgacg gcggcccaga gtcgcaccac ccacaaggat | 1140 |

```
ctggcgatcc tgtcccggct gatgctggtg atcgcggagc acctgcgcga cgaataccte    1200 ggcatccact acgcgaaggc gcagaacctg cggctggagc tcggcaagca gatcgacgcc    1260
gtcctccagg accgggctgc actgctgacc ccgaccacgc ctaccgttgc caacgagctg    1320
ttgagcggtc ggcaagacac catgtccatg atcccacgga tgacgggcaa tgcgatcctc    1380
aacacgtgcc cgctggacct caccggtcac ccggcgctga cggtgcccac gggtgcgggc    1440
gagaagggcc tgcccgttgg cctccaagtg ataggccgcc acttcgagga gtcgacgctc    1500
taccgcaccg gcgccgtgat cgaggccgcc ggcctatggg agctcgccgc ggagccgagc    1560
gcaccggtgc tgcggtag                                                  1578
```

METHOD FOR METABOLIZING CARBAZOLE IN PETROLEUM

CROSS-REFERENCE TO RELATED APPLICATION

This application claims the benefit of an earlier filed provisional application having Ser. No. 60/409,562 and a Filing Date 10 Sep. 2002.

The U.S. Government has a paid-up license in this invention and the right in limited circumstances to require the patent owner to license others on reasonable terms as provided for by the terms of Contract No. DE-AC26-99BC 15219 awarded by the U.S. Department of Energy.

BACKGROUND OF THE INVENTION

1. Field of the Invention

This invention relates to a bacterial culture having the ability to metabolize the nitrogen-containing heterocycle carbazole and a method for removing nitrogen from nitrogen-containing solid and liquid hydrocarbon and carbonaceous materials. More particularly, this invention relates to the use of a culture of *Sphigomonas sp.* having the capability of expressing a carbazole degradation trait constitutively for the removal of carbazole from solid and liquid hydrocarbon and carbonaceous materials including, but not limited to, shale oil, crude oil, petroleum products, coal tar and mixtures thereof and for the selective cleavage of C—N bonds in such solid and liquid hydrocarbon and carbonaceous materials.

2. Description of Related Art

Heavy crude oils and residuum constitute a significant and ever-increasing portion of the world petroleum reserves. These heavy oils possess high calorific content yet have comparatively low market values chiefly because of high sulfur, nitrogen and metals content, high viscosity and molecular weight. The presence of nitrogen-containing compounds and associated metals in petroleum can contribute to inactivation of catalysts in hydrotreating and catalytic cracking processes, thereby causing a decreased efficiency of these refinery operations. The problems associated with heavy oils have prompted the preferential utilization of light crude oils. As light crude oils are consumed at a disproportional rate, the amount of heavy oil as a percentage of remaining or world petroleum reserves continues to escalate.

New technologies capable of dealing with heavy oils to mitigate environmental concerns and to allow processing in conventional refineries in a cost-effective manner are needed. Biorefining is one such technique.

Carbazole is a nitrogen-containing heterocycle that is one of the main components of shale oil, crude oil, petroleum products and coal tar. In addition, carbazole is frequently used in the production of dyes, medicines and plastics. The combustion of crude oil transforms nitrogen therein into nitrogen oxides which, when released into the atmosphere, contribute to the formation of acid rain. Nitrogen compounds and associated metals in petroleum can also deactivate catalysts used in oil refineries and can contribute to the chemical instability of refined petroleum products. Accordingly, there is a need for methods for removing nitrogen from petroleum in order to protect the environment and to allow refineries to maximize efficiency.

A variety of bacterial cultures that possess the ability to selectively remove sulfur from organosulfur compounds such as dibenzothiophene have been described and a biochemical pathway for the selective cleavage of carbon-sulfur bonds is known. The use of biodesulfurization to selectively remove sulfur from petroleum and coal while retaining the fuel value has been demonstrated. No such similar pathway is known for the selective cleavage of carbon-nitrogen bonds.

A variety of carbazole-degrading microorganisms are known to exist including *Sphigomonas* CDH-7, *Sphingomonas sp.* CB3, *Pseudomonas resinovorans* CA10, *Pseudomonas* CA06, *Pseudomonas* OM1, *Pseudomonas* LD2, *Mycobacterium, Ralstonia, Xanthamonas* and *Sphigomonas* KA1. To the extent that these differing species of carbazole degraders have been studied, it appears as if they all follow a similar carbazole degradation pathway that begins with the oxidative cleavage of the hetercyclic nitrogen ring of carbazole to form 2-aminobiphenyl-2,3-diol. Thus, the initial step in the metabolism of carbazole, catalyzed by carbazole 1, 9a-dioxygenase (CARDO), results in the cleavage of one of the two carbon-nitrogen bonds. However, subsequent biodegradation of carbazole by all cultures characterized heretofore involves degradation of one of the aromatic rings. Most carbazole degrading cultures produce both 2-hydroxypenta-2,4-dienoate and 2-aminobenzoate (anthranilic acid). 2-aminobenzoate undergoes cleavage of the amino substituent to yield catechol that subsequently enters the tricarboxylic acid cycle.

Some carbazole-degrading cultures, like *Sphigomonas sp.* CB3, have been found to contain carbazole dioxygenases that are related to biphenyl oxidases while other cultures, such as *P. resinovorans* CA10 (GenBank Accession No. D89064), contain carbazole dioxygenases that show no close relationship to other characterized oxidases (Shepherd, J. M. et al., "Novel Carbazole Degradation Genes in *Sphigomonas* CB3: Sequence Analysis, Transcription, and Molecular Ecology", *Biochemical and Biophysical Research Communications*, 247, 129–135 (1998)). CARDO consists of three components: a dioxygenase, ferredoxin, and ferredoxin reductase. The genes encoding CARDO in *Sphigomonas sp.* CB3 are contiguous, while in *P. resinovorans* CA10 they are not. The dioxygenase from *Sphingomonas sp.* CB3 consists of two subunits, as contrasted with the single subunit present in *P. resinovorans* CA10. Additionally, the carbazole dioxygenase enzyme of *Sphigomonas sp.* CB3 has a rather narrow substrate range and does not metabolize naphthalene, dibenzothiophene, phenanthrene or fluorene, unlike *P. resinovorans* CA10 (Nojiri, H. et al., Diverse Oxygenations Catalyzed by Carbazole 1,9a-Dioxygenase from *Pseudomonas sp.* Strain CA 10", *Journal of Bacteriology*, Vol. 181, No. 10, pp. 3105–3113 (May 1999)). The carbazole-degradation phenotype of previously characterized cultures is induced when carbazole is added to the growth medium and genes responsible for anthranilate conversion to catechol are suggested to be induced by carbazole as well (Shepherd, J. M. et al., supra; Nojiri, H. et al., "Organization and Transcriptional Characterization of Catechol Degradation Genes Involved in Carbazole Degradation by *Pseudomonas resinovorans* Strain CA10", *Biosci. Biotechnol. Biochem.*, 66 (4), 897–901, (2002); Kirimura, K. et al., "Selective and Continuous Degradation of Carbazole Contained in Petroleum Oil by Resting Cells of *Sphigomonas sp.* CDH-7", *Biosci. Biotechnol. Biochem.*, 63 (9), 1563–1568 (1999); Habe, H. et al., "*Sphigomonas sp.* Strain KA1, Carrying a Carbazole Dioxygenase Gene Homologue, Degrades Chlorinated Dibenzo-p-dioxins in Soil", *FEMS Microbiology Letters*, 211, 43–49 (2002)).

SUMMARY OF THE INVENTION

It is one object of this invention is to provide a biochemical pathway for the selective cleavage of C—N bonds.

It is another object of this invention to provide microorganisms possessing this pathway which can then be used to reduce the nitrogen concentration of fossil fuels.

It is another object of this invention to provide a microorganism having the ability to biodegrade carbazole.

It is another object of this invention to provide a method for the biodegradation of carbazole.

It is yet another object of this invention to provide microorganisms which can be used as a tool in organic chemistry in applications where cleavage (or synthesis) of a C—N bond would be beneficial.

It is still a further object of this invention to provide a microorganism suitable for cleaving C—N bonds in carbazole while leaving the C—C bonds intact.

It is yet a further object of this invention to provide a method for cleaving C—N bonds in carbazole while leaving the C—C bonds intact.

The invention disclosed herein involves the isolation of a new bacterium, *Sphigomonas sp.* GTIN11 (ATCC BAA-487), that expresses a carbazole degradation trait constitutively, a method for degrading carbazole using this bacterium and a new biochemical pathway for the selective cleavage of C—N bonds. The DNA sequence of the genes in *Sphigomonas sp.* GTIN11 that encode enzymes for the cleavage of one of the C—N bonds in carbazole is GenBank Accession No. AF442494. Because of the ability to express the carbazole degradation trait constitutively, the bacterium can grow in complex rich nutrient medium yielding rapid growth and carbazole degradation rates. The majority of the genes required for carbazole degradation were cloned and characterized. The enzymes involved in carbazole degradation in *Sphigomonas sp.* GTIN11 show less than or equal to about 61% similarity to the carbazole enzymes present in other carbazole degradation competent cultures. To the best of our knowledge, prior to this invention, carbazole-degrading cultures having the ability to treat petroleum have not been demonstrated, described or reported.

In accordance with one embodiment of the invention claimed herein, carbazole degradation is achieved by contacting a microbial strain capable of expressing a carbazole trait constitutively with carbazole, resulting in degradation of at least a portion of said carbazole. Although any microbial strain expressing a carbazole trait constitutively may be used, a preferred microbial strain is *Sphigomonas sp.* GTIN11.

BRIEF DESCRIPTION OF THE DRAWINGS

These and other objects and features of this invention will be better understood from the following detailed description taken in conjunction with the drawings wherein.

DETAILED DESCRIPTION OF THE PRESENTLY PREFERRED EMBODIMENTS

Figure 1:
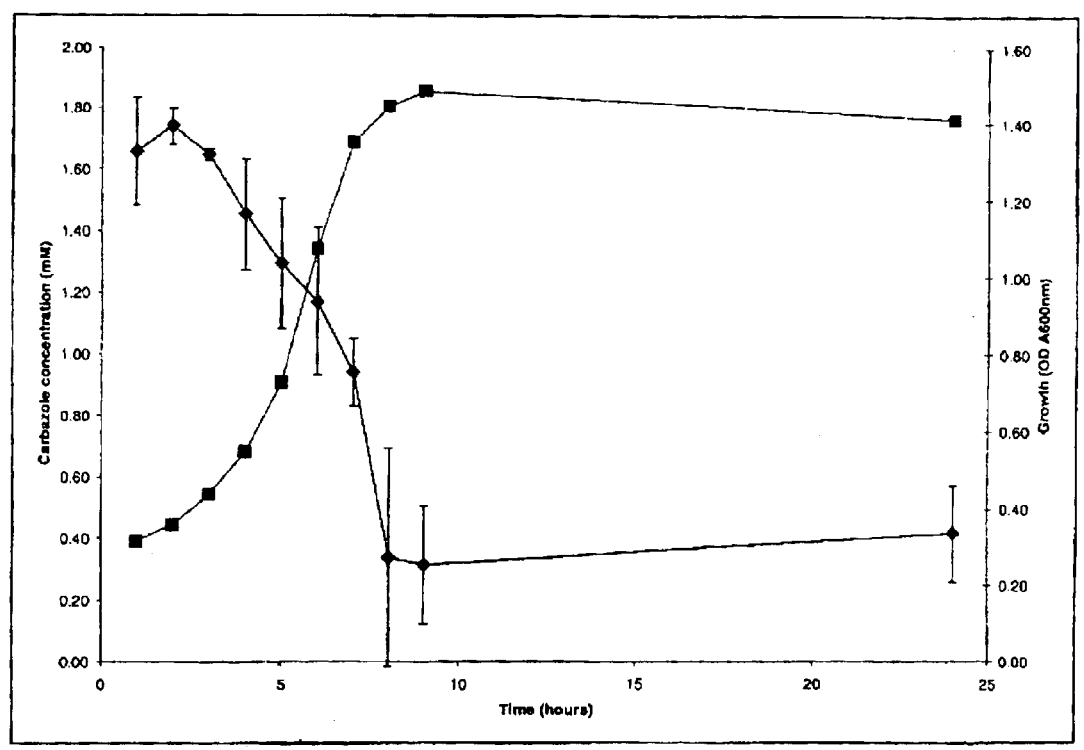
FIG. 1 is a graphical representation showing the growth of *Sphigomonas sp.* GTIN11 in nutrient rich TT media and carbazole degradation.

A bacterial culture suitable for use in the method of this invention was isolated from a manufactured gas plant soil based on its ability to metabolize the nitrogen-containing heterocycle carbazole. The culture (ATCC No. BAA-487) was identified as a *Sphigomonas sp.* based upon the DNA sequence of a portion of its 16rRNA gene (GenBank Accession No. AY056468) and was given the designation GTIN11. A cloned 4.2 kb DNA fragment was confirmed to contain genes responsible for carbazole degradation. DNA sequence analysis revealed that the fragment contained five open reading frames (ORFs) with the deduced amino acid sequence showing homology to carbazole terminal dioxygenase (ORF1), 2,3-dihydroxybiphenyl dioxygenase subunits (ORF2 and ORF3), meta-cleavage compound hydrolases (ORF4) and ferredoxin component of bacterial multicomponent dioxygenases (ORF5). The percent similarity was 61% of these proteins or less to known proteins. The specific activity of *Sphigomonas sp.* GTIN11 (ATCC No. BAA-487) for the degradation of carbazole at 37° C. was determined to be 8.0 μmole carbazole degraded/min/g-dry cell weight. This strain is unique in expressing the carbazole degradation trait constitutively. Resting cells of *Sphigomonas sp.* GT11 removed 95% of carbazole and 50% of C1-carbazoles from petroleum in a 16-hour treatment time.

Culture isolation and characterization of *Sphigomonas sp.* GTIN11 was carried out as follows. A turbidostat was operated at 37° C. using A2 medium and carbazole as the sole source of nitrogen. Medium A2 is a nitrogen-free medium comprising 5.0 g glucose, 6.3 g $KH_2PO_4$, 8.0 g $K_2HPO_4$, 0.2 $MgSO_4$, 1.0 ml vitamin solution and 2.0 metal solution per liter. The vitamin solution contains 400 mg Ca-pantothenate, 400 mg niacin, 400 mg pyridoxine-HCL, 200 mg inositol, 200 mg p-aminobenzoate, 200 mg D-biotin, 50 mg riboflavin, 50 mg folic acid, 15 mg thiamine HCL and 50 mg cyanocobalamin per liter of distilled water. The metal solution contains 100 mg $MnSO_4$, 31.7 mg $CuCl_2$, 25 mg $(NH_4)_6Mo_7O_{24}$, 20 mg $H_3BO_3$, 25 mg $Co(NO_3)_2$, 25 mg $ZnCl_2$ and 10 mg $NH_4VO_3$ per liter of distilled water. Nitrogen, either an ammonium salt or an organic compound, was added at concentrations ranging from 0 to 1 mM. The turbidostat was inoculated with samples obtained from manufactured gas plant soils where chronic hydrocarbon contamination exists. A carbazole degrading strain was obtained by periodic screening of the turbidostat culture supernatent for the ability to grow on carbazole as the sole source of nitrogen. Initially, a mixed culture was obtained; however, after streaking the mixed culture onto TT agar and A2-carbazole agar plates, individual colonies were isolated and eventually a pure culture capable of growing in medium A2 with carbazole as the sole nitrogen source was obtained.

The culture thus obtained is a facultative Gram-negative rod that forms medium sized, smooth, beige, round colonies with regular and complete margins on TT agar. Positive results indicating that the culture utilizes glucose, rhamnose, melibiose and arabinose were obtained with the API20E bacterial identification system, while all other tests were negative. The culture is oxidase negative and capable of both oxidizing and fermenting glucose as determined by the API OF test. An alignment of the 472 bp DNA sequence of the 16S rDNA of the culture with DNA sequences available in the MIDI Labs and GenBank database indicate that it is most closely related to *Sphingomonas chlorophenolica* (98.51% homology) and *Sphingomonas yanoikuyae* (97.24% homology). These data indicate that this carbazole-degrading bacterium can be identified to the genus level as a *Sphingomonas*. Based upon these results, the culture was designated as *Sphigomonas sp.* GTIN11. The partial 16S rRNA gene sequence for the strain *Sphigomonas sp.* GTIN11 is available from GenBank under Accession Number AY056468. The partial carbazole degradation operon nucleotide sequence for the strain *Sphigomonas sp.* GTIN11 is available from GenBank under Accession Number AF442494.

The microbial strain Sphigomonas sp. GTIN11 obtained as described above exhibited 2,3-dihydroxybiphenyl dioxygenase activity on rich nutrient medium, suggesting constitutive expression of the carbazole degradation trait. ATCC medium 697 or TT rich medium comprises 8.0 g polypeptone, 4 g yeast extract and 2 g NaCl. Growth of the strain Sphigomonas sp. GTIN11 in TT medium at 37° C. was observed to be rapid with a generation time of 2.1 hours as shown in FIG. 1. The presence or absence of carbazole in TT medium does not affect the growth rate of Sphingomonas sp. Moreover, as shown in FIG. 1, the culture growing in TT medium is capable of metabolizing carbazole, decreasing the concentration from 1.7 mM to 0.3 mM (82% degradation) within about 8 hours. No further degradation of carbazole was observed once the cells entered the stationary phase of growth. The growth of Sphigomonas sp. GTIN11 in medium A2 was observed to be much slower than in TT medium with a generation time of 16 hours using either carbazole or ammonia as sole sources of nitrogen.

Sphigomonas sp. GTIN11 resting cell specific activity for carbazole degradation averaged 8.0 μmol/min/g dry cell weight (DCW) compared to an estimated 10 μmol/min/g DCW for Sphigomonas sp. CDH-7 (Kirimura, K. et al., supra). However, Sphigomonas sp. GTIN11 is unique in expressing the carbazole degradation phenotype constitutively, allowing active cell suspensions to be obtained from rapidly growing cultures in TT medium. Sphigomonas sp. GTIN11 was also grown in minimal medium A2 using ammonia as a nitrogen source and a variety of carbon sources, e.g. glucose, sucrose, acetate, fumurate, succinate and lactate. The specific activity remained the same for TT and minimal media grown Sphingomonas sp. GTIN11 cells. Routine cultivation of Sphigomonas sp. GTIN11 on medium A2 with the addition of carbazole as the sole carbon or nitrogen source was required to maintain the carbazole phenotype and high specific activity rates.

Figure 2:
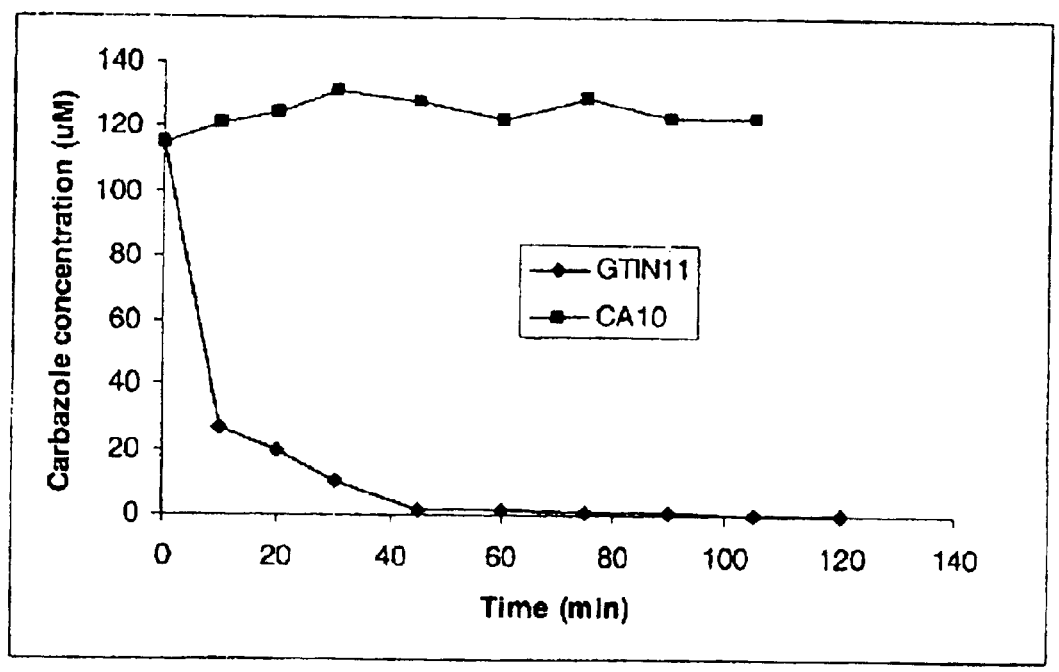
FIG. 2 is a graphical representation showing the results of TT pre-grown cell preparations of *Sphigomonas sp.* GTIN11 and *P. resinovorans* CA10 exposed to 120 μM carbazole for 120 minutes.

To confirm constitutive expression of the carbazole degradation trait of GTIN11, we examined the ability of the cells to metabolize carbazole after growth in liquid culture on a rich nutrient medium (TT) using both Sphigomonas sp. GTIN11 and P. resinovorans CA10. Cultures were grown in TT medium until 0.7 to 0.9 OD at A600 nm, the cells were concentrated and washed in 50 nM HEPES, 120 μM unlabelled carbazole and $1 \times 10^6$ DPM of $^{14}C$ carbazole were added and the cells were incubated for 120 minutes at 30° C. The cultures were extracted and analyzed by HPLC, the results of which are shown in FIG. 2. Sphigomonas sp. GTIN11 metabolizes carbazole after growth on rich nutrient media while P. resinovorans CA10 does not. The complete degradation (mineralization) of $^{14}C$ carbazole to $CO_2$ and $H_2O$ was also monitored. Approximately $4.5 \times 10^5$ DPM $^{14}CO_2$ was recovered from the Sphigomonas sp. GTIN11 flask while no $^{14}CO_2$ was recovered from the P. resinovorans CA10 flask.

To identify the metabolic pathway of carbazole degradation by Sphigomonas sp. GTIN11, extracts of both growing and resting cells that were exposed to carbazole were analyzed by GC-MS. The results obtained indicated only the presence of metabolites that had undergone substantial biodegradation. Metabolites of carbazole that were detected in Sphigomonas sp. GTIN11 culture supernatants included anthranilic acid, succinic anhydride, succinic acid and fumaric acid. Anthranilic acid has been detected as a metabolite of carbazole produced by other cultures from which we conclude that Sphigomonas sp. GTIN11 probably follows a similar, if not identical, pathway. However, because metabolites derived from early steps in the pathway were not detected, this remains a speculation, although anthranilic acid can be employed as a carbon source by Sphigomonas sp. GTIN11.

Growth tests were performed to determine the range of organonitrogen compounds that can serve as sole sources of nitrogen for Sphigomonas sp. GTIN11. Of the organonitrogen compounds tested, carbazole was the only organonitrogen compound that supported healthy growth of this culture. Sparce growth was obtained with 2-methyl carbazole. The ability of Sphigomonas sp. GTIN11 to metabolize compounds structurally related to carbazole was further investigated by incubating resting cells in the presence of various compounds for 16 hours at 37° C. and then analyzing the results using thin layer chromatography (TLC). The results were similar to the results obtained using purified carbazole 1,9a-dioxygenase from P. resinovorans CA10.

Cloning and characterization of the genes involved in carbazole degradation was carried out as follows. Colonies of E. coli DH5α containing recombinant pUC18 with a library of cloned fragments from the Sphigomonas sp. GTIN11 chromosome were screened for the expression of 2,3-dihydroxybiphenyl dioxygenase. As a result of screening, a plasmid containing a 4.2 kb insert was isolated, sequenced and submitted to GenBank under accession number AF442494. The fragment contained five open reading frames relevant to carbazole degradation. Each open reading frame was initiated by either ATG or GTG and was preceded by potential ribosome binding sites (RBS). Immediately preceding the start site of the first open reading frame nucleotide sequence were two putative prokaryotic promoters at nucleotide positions 426 to 471 (Score=0.85) and at positions 507 to 552 (Score=0.94) as determined by promoter prediction by neural network (NNPP) at BCM search launcher (http://searchlauncher.bcm.tmc.edu). About 1 kb of DNA sequence 5' relative to the first open reading frame was also determined, but no genes relevant to carbazole degradation were detected. A portion of the upstream region has homology (54%) to GntR-family transcriptional regulators, but it is in the opposite orientation relative to the first open reading frame.

TABLE 1

| ORF | Deduced Protein feature | Nucleotide Position | No. of aa | Predicted molecular mass (Kda) | % Similarity to Other Gene Products (% similarity, gene name, strain) |
|---|---|---|---|---|---|
| ORF1 | Carbazole dioxygenase CarAa | 650–1786 | 378 | 42.6 | 60: carAa (Pseudomonas CA10) 41: OXOO (Pseudomonas putida 86) 22: CAO (Chlamydomonas reinhardtii) 21: carA (Sphingomonas sp. CB3) |
| ORF2 | meta cleavage enzyme subunit CarBa | 1735–2067 | 110 | 12 | 36: carBa (Pseudomonas resinovorans CA10) |
| ORF3 | meta cleavage enzyme catalytic | 2060–2863 | 267 | 28.9 | 43: carBb (Pseudomonas resinovorans CA10) |

TABLE 1-continued

| ORF | Deduced Protein feature | Nucleotide Position | No. of aa | Predicted molecular mass (Kda) | % Similarity to Other Gene Products (% similarity, gene name, strain) |
|---|---|---|---|---|---|
| | subunit CarBb | | | | 31: PHNC (Burkholderia sp. RP007) 29: FLDU (Sphingomonas sp. LB126) |
| ORF4 | meta cleavage compound hydrolase CarC | 2906–3730 | 274 | 29.6 | 57: carC (Pseudomonas resinovorans CA10) 45: DXNB (Sphingomonas sp. RW1) 36: NAHN (Pseudomonas sp. AN10) 32: carD (Sphingomonas sp. CB3) |
| ORF5 | ferredoxin CarAc | 3771–4100 | 109 | 11.5 | 50: FDVI (Rhodobacter capsulatus) 50: FDXE (Rhodobacter capsulatus B10) 47: MSL0793 (Rhizobium meliloti) |

Legend Table 1 -
Bacterial Strains and GenBank Accession Numbers
of Corresponding Genes:

*Sphigomonas sp.* strain CB3 (AF060489)
*P resinovorans* CA10 (D89064/D89065)
*Pseudomonas putida* 86 (Y12655)
*Chalmydomonas reinhardtii* (AB0151390)
*Streptomyces coelicolor* A3 (2) (AL021529)
*Burkholderia sp.* RP007 (AF061751)
*Sphingomonas sp.* LB126 (AJ277295)
*Sphingomonas sp.* RW1 (X72850)
*Pseudomonas sp.* AN10 (X52805)
*Rhodobacter capsulatus* ATCC 33303/B10 (Y545612)
*Rhodobacter capsulatus* B10 (Y11304)
*Rhizobium meliloti* MAFF303099 AP002995)
Gene codes in descending order carAa = carbazole dioxygenase
OXOO = 2-oxo-1,2-dihydroquinoline 8-monooxygenase
CAO = chlorophyll A oxidase
carA = carbazole dioxygenase
carBa = meta cleavage enzyme
PHNC = extradiol dioxygenase
FLDC = putative protocatechuate dioxygenase
carC = meta cleavage compound hydrolase
DXNB = hydrolase
NAHN = hydroxymuconic semialdehyde hydrolase
carD = hydrolase
FDVI = ferredoxin
FDXE = ferredoxin
MSL0793 = ferredoxin Table 1 shows the deduced protein feature, nucleotide position, number of amino acids, predicted molecular mass (Kda) and percent similarity to the other gene products of the open reading frames believed to encode genes from the carbazole operon of GTIN11. Table 1 includes the percent similarity (>20%) of the GTIN11 gene products to two other carbazole degrading microorganisms, *P. resinovorans* CA10 and *Sphigomonas sp.* CB3, for which sequence information is available. The data in Table 1 indicate that the proteins of the carbazole degradation pathway of *Sphigomonas sp.* GTIN11 show ≦60% similarity to other known proteins.

The first open reading frame (ORF1) encodes a 42.6 kDa protein that most closely resembles, with 60% similarity, the CARDO terminal dioxygenase subcomponent (CarAa) from *P. resinovorans* CA10. This protein was designated CarAa. A 2-oxo-1, 2-dihydroquinoline 8-monooxygenase and a chlorophyll A oxidase have more similarity to *Sphigomonas sp.* GTIN11 CarAa protein (41% and 22%, respectively) than the *Sphigomonas sp.* CB3 carbazole dioxygenase.

The second and third open reading frames (ORF2 and ORF3, respectively) encode for two proteins that are similar to the two components, CarBa and CarBb, of 2-aminobiphenyl-2,3-diol 1,2-dioxygenase from *P. resinovorans* CA10, respectively. The CarBa protein from GTIN11 showed no significant similarity with any other protein in the database except the CarBa enzyme from *P. resinovorans* CA10, whereas the CarBb protein from GTIN11 showed similarity to both the CarBb enzyme of *P. resinovorans* CA10 and other protocatechuate dioxygenases. The fourth open reading frame (ORF4) encodes an enzyme that has similarity with hydrolases involved in the degradation of monocyclic aromatic compounds and is most closely related to the CarC enzyme from *P. resinovorans* CA10. The fifth open reading frame (ORF5) encodes for a ferredoxin enzyme believed to be a subunit, based upon gene arrangement similarity to CA10, of carbazole dioxygenase and was designated CarAc (SEQ ID NO. 2). All the carbazole degradation enzymes of GTIN11 except CarAc are the most similar to the carbazole degradation enzymes from *P. resinovorans* CA10 and proteins involved in the degradation of aromatic compounds. However, when DNA sequence data is analyzed, the CarAa (SEQ ID NO. 1) and carC genes of *Sphigomonas sp.* GTIN11 show 64% and 65% homology, respectively, to the corresponding genes in *P. resinovorans* CA10. The carBa and carBb genes of GTIN11 are 58% homologous to a *Pseudomonas paucimobilis* protocatechuate 4,5-dioxygenase gene (M34835), while no significant DNA homology was found to any sequences in the GenBank database for the GTIN11 carAc gene.

An 1100 bp PCR fragment of *Sphigomonas sp.* KA1 containing portions of two genes suspected to be involved in carbazole metabolism has been published in GenBank, Accession Number AB072827. We believe these genes may be involved in carbazole metabolism in this strain because they encode proteins similar to *P. resinovorans* CA10 CarA and CarB proteins. While the carAc and carBa genes present in *Sphigomonas sp.* KA1 are 100% homologous to the *Sphingomonas sp.* GTIN11 genes isolated and described herein, the 16S rRNA gene sequences of these two strains are different.

Through phylogenetic analysis of the 16S rRNA sequences (*Sphigomonas sp.* KA1-Accession Number AB064271) from these two strains, we have confirmed that these two organisms are unique *Sphingomonads*. The presence of identical carAa and carBa genes in two different *Sphigomonas* strains isolated from vastly different samples and geological regions suggest that genetic transfer of the genes responsible for carbazole metabolism is possible.

*Sphigomonas sp.* GTIN11 resembles *P. resinovorans* CA10 in that the terminal oxidase component of CARDO is a single subunit rather than the two subunits found in *Sphigomonas sp.* CB3. Moreover, the arrangement of genes in the carbazole operon of *Sphigomonas sp.* GTIN11 most closely resembles that of *P. resinovorans* CA10 except that two copies of the carAa gene are present in *P. resinovorans*. The 4.2 kb HindIII fragment did not contain a ferredoxin reductase component that is required for activity of the dioxygenase activity and the *E. coli* DH5α/pUC 18 GTIN11 HindIII construct does not have the ability to use carbazole.

To confirm the involvement in carbazole biodegradation of the genes contained on the 4.2 kb fragment derived from *Sphigomonas sp.*, we created a mutant strain of *Sphigomonas sp.* GTIN11 deficient in the carbazole phenotype by disrupting carAa with a kanamycin resistance ($Km^R$) gene. A 2.0 kb PCR PstI fragment containing a region spanning three separate genes, carAa, carBa and carBb, was derived from the 4.2 kb pUC18-HindIII GTIN11 chromosome library plasmid and cloned into pUC18. This construct was then digested with BstBI, a 4566 bp fragment purified from an agarose electrophoresis gel and ligated to itself. This procedure removes a 132 bp fragment in carAa. The resulting construct was digested with BstBI and a kanamycin resistance cassette ($Km^R$) from EZTN (Tn903) was ligated into the BstBI site to create pCAR-Km. This vector can replicate in *E. coli* but not in GTIN11. However, through homologous recombination between the carA and carB gene sequences, pCAR-Km integrates into the chromosome when it is used to transform GTIN11. Transformants were screened at 35° C. on TT rich medium supplemented with kanamycin (20 μg/ml). The kanamycin resistant colonies of *Sphigomonas sp.* GTIN11 containing an interrupted carAa gene were confirmed by HPLC analysis to be defective in carbazole metabolism.

TABLE 2

| SAMPLE | Carbazole (μg/ml) | Carbazole Removal (%) |
| --- | --- | --- |
| Untreated Control | 427 | |
| Untreated Control | 416 | |
| P.CA10 (700.8 mg DCW) | 510 | |
| P.CA10 (703.2 mg DCW) | 500 | |
| GTIN11-A (732 mg DCW) | 53.5 | 87.3 |
| GTIN11-A (732 mg DCW) | 60.9 | 87.9 |
| GTIN11-B (648 mg DCW) | 36.5 | 91.3 |
| GTIN11-B (648 mg DCW) | 40.7 | 91.9 |
| GTIN11-C (2,560 mg DCW)* | 24.9 | 94.1 |
| GTIN11-C (2,560 mg DCW)* | 26 | 94.5 |

*= biotreatment experiments employed 3 grams of shale oil exposed to an aqueous cell suspension of 50 ml; all other biotreatments utilized 2 grams of shale oil and 25 ml of cell suspension containing the indicated dry cell weight (DCW) amounts While *Sphigomonas sp.* GTIN11 has been shown to metabolize carbazole in experiments employing model compounds, we also conducted experiments to determine if similar results would be obtained using petroleum, where a complex mixture of chemicals is present and exposure to petroleum could be potentially damaging to biocatalysts. The results in Table 2 illustrate that *Sphigomonas sp.* GTIN11 is capable of removing carbazole from shale oil, and that nearly complete removal can be achieved when higher biomass-to-oil ratios are used. Carbazole removal was determined by using GC-MS and new peaks representing carbazole metabolites were not observed. The better carbazole removal efficiency seen with samples GTIN11-B in Table 2 versus samples GTIN11-A, even though it has a slightly lower biomass concentration, may be due to a slight difference in the specific activity of the various cell preparations used in these experiments. GC-MS analyses of biotreated shale oil samples indicated that alkylated derivatives of carbazole were also degraded. Carbazole derivatives containing a single methyl group substitution showed as much as 50% reduction, while no degradation was apparent with more heavily substituted carbazole derivatives.

In summary, enrichment culture experiments employing carbazole as the sole source of nitrogen resulted in the isolation of *Sphigomonas sp.* GTIN11, a unique strain that encodes a carbazole degradation pathway similar to previously characterized carbazole-degrading cultures. *Sphigomonas sp.* GTIN11 is unique in expressing the carbazole degradation phenotype constitutively. Protein homology and the organization of genes indicate that the carbazole operon of *Sphigomonas sp.* GTIN11 is most closely related to *P. resinovorans* CA10, but differs significantly as proteins are ≦60% similar. The essentially complete removal of carbazole from petroleum was demonstrated using *Sphigomonas sp.* GTIN11. However, the carbazole degradation pathway does not selectively remove nitrogen from carbazole. Rather, carbazole is either converted to water-soluble metabolites or degraded completely. It would be preferable if a pathway that selectively removes nitrogen from carbazole while leaving the rest of the molecule intact, analogous to the dsz pathway for the removal of sulfur from DBT by *Rhodococcus erythropolis,* could be isolated or constructed.

We have also discovered that combining the carAa, carAc and carAd genes of *Sphigomonas sp.* GTIN11 and/or the carAd gene of *Pseudomonas resinovorans* CA10 (SEQ ID NO. 3), which encode for enzymes responsible for the conversion of carbazole to 2-aminobiphenyl-2,3-diol, as previously discussed, with a gene encoding an amidase (e.g. amdA gene from *Rhodococcus erythropolis* MP50) capable of selectively cleaving the C—N bond in 2-aminobiphenyl-2,3-diol or a melamine amidase encoded by the triA gene of *Pseudomonas sp.* NRRLB-12227 (GenBank Accession No. AF312304) results in the creation of an operon that encodes for the cleavage of both C—N bonds in carbazole. Mutagenizing the amdA or triA genes, forming derivative amidase genes, in bacterial hosts that also contain carA genes and selecting for growth with carbazole as the sole nitrogen source produces certain derivative cultures. The original amidases will not recognize 2-aminobiphenyl-2,3-diol as a substrate, but mutant derivatives that do metabolize 2-aminobiphenyl-2,3-diol will liberate ammonia nitrogen, thereby enabling growth of the bacterial host in nitrogen-limited/deficient media. In the event that a carbazole-degrading culture such as *Sphigomonas sp.* GTIN11 is employed as the host to contain this C—N cleavage operon, the carB and/or other carbazole degradation genes should be inactivated by deletion or insertion mutagenesis so that degradation of carbazole is no longer possible. Alternatively, a bacterial host that never contained the ability to degrade carbazole, such as *E. coli,* may be used as the host for the expression of the C—N bond cleavage pathway, thereby ensuring that only C—N bond cleavage and not carbazole degradation can take place. Cell suspensions of cultures containing the C—N bond cleavage pathway are then used to contact petroleum or model compound samples to accomplish the selective cleavage of C—N bonds in carbazole and related chemical structures. Incubation at 30° C. with shaking for 16 hours is employed, although shorter times may also be employed.

By way of example, a bacterial culture containing the C—N specific degradation pathway was incubated in the presence of petroleum. One gram dry weight of cells were suspended in 10 ml of bacterial growth medium and then incubated with 2 grams of petroleum (shale oil) at 30° C. with shaking for 16 hours. The result was a reduction in the concentration of carbazole present in the petroleum sample of 95%.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A biologically pure culture comprising:
   a biochemical pathway comprising an operon that encodes for selective cleavage of both C—N bonds of carbazole, said operon comprising a carAa gene (SEQ ID NO. 1) and a carAc gene (SEQ ID NO. 2) from *Sphingomonas* sp. ATCC No. BAA-487 and a carAd gene (SEQ ID NO. 3) from at least one of said *Sphingomonas* sp. ATCC No. BAA-487 and *Pseudomonas resinovorans* CA10.

2. A biologically pure culture in accordance with claim 1, wherein said operon comprises at least one additional gene capable of selectively cleaving the C—N bond in said 2-aminobiphenyl-2,3-diol.

3. A biologically pure culture in accordance with claim 2, wherein said at least one additional gene capable of cleaving the C—N bond in said 2-aminobiphenyl-2,3-diol encodes an amidase capable of selective cleavage of the C—N bond of said 2-aminobiphenyl-2,3-diol.

4. A biologically pure culture in accordance with claim 3, wherein said at least one additional gene is an amdA gene (SEQ ID NO. 4) from *Rhodococcus erythropolis* MP50.

5. A biologically pure culture in accordance with claim 1, wherein said operon comprises one of an amdA gene (SEQ ID NO. 4) from *Rhodococcus erythropolis* MP50 and a triA gene of *Pseudomonas* sp. NTTLB-12227 (GenBank Accession No. AF312304).

* * * * *

UNITED STATES PATENT AND TRADEMARK OFFICE
CERTIFICATE OF CORRECTION

PATENT NO. : 6,943,006 B2  Page 1 of 1
APPLICATION NO. : 10/658691
DATED : September 13, 2005
INVENTOR(S) : Kayser et al.

It is certified that error appears in the above-identified patent and that said Letters Patent is hereby corrected as shown below:

Title Page, Item (73),

Assignee, delete "Alps Electric Co., Tokyo (JP)", and in its place insert --Gas Technology Institute, Des Plaines, Illinois--

Title Page, Item (74),

Attorney, Agent, or Firm, delete "Brinks Hofer Gilson & Lione", and in its place insert --Mark E. Fejer--

Signed and Sealed this

Tenth Day of October, 2006

JON W. DUDAS
*Director of the United States Patent and Trademark Office*